United States Patent
Lenzi et al.

(10) Patent No.: US 10,213,324 B2
(45) Date of Patent: Feb. 26, 2019

(54) MINIMUM JERK SWING CONTROL FOR ASSISTIVE DEVICE

(71) Applicant: Rehabilitation Institute of Chicago, Chicago, IL (US)

(72) Inventors: Tommaso Lenzi, Chicago, IL (US); Levi Hargrove, Chicago, IL (US); Jon Sensinger, Fredericton (CA)

(73) Assignee: Rehabilitation Institute of Chicago, Chicago, IL (US)

(*) Notice: Subject to any disclaimer, the term of this patent is extended or adjusted under 35 U.S.C. 154(b) by 0 days.

(21) Appl. No.: 14/839,309

(22) Filed: Aug. 28, 2015

(65) Prior Publication Data

US 2016/0058582 A1 Mar. 3, 2016

Related U.S. Application Data

(60) Provisional application No. 62/043,213, filed on Aug. 28, 2014, provisional application No. 62/049,686, filed on Sep. 12, 2014.

(51) Int. Cl.
| | |
|---|---|
| *A61F 2/66* | (2006.01) |
| *A61F 2/70* | (2006.01) |
| *A61F 2/76* | (2006.01) |
| *A61F 2/60* | (2006.01) |
| *A61F 2/68* | (2006.01) |
| *A61F 2/64* | (2006.01) |

(52) U.S. Cl.
CPC ................. *A61F 2/70* (2013.01); *A61F 2/60* (2013.01); *A61F 2/68* (2013.01); *A61F 2/64* (2013.01); *A61F 2/66* (2013.01); *A61F 2/6607* (2013.01); *A61F 2002/701* (2013.01); *A61F 2002/704* (2013.01); *A61F 2002/762* (2013.01); *A61F 2002/764* (2013.01); *A61F 2002/7615* (2013.01); *A61F 2002/7625* (2013.01); *A61F 2002/7635* (2013.01)

(58) Field of Classification Search
CPC .................................................. A61F 2002/704
See application file for complete search history.

(56) References Cited

U.S. PATENT DOCUMENTS

| | | | | |
|---|---|---|---|---|
| 7,147,667 | B2* | 12/2006 | Bedard | A61F 2/644 623/24 |
| 7,867,284 | B2* | 1/2011 | Bedard | A61F 2/644 623/24 |
| 10,031,524 | B2* | 7/2018 | Su | B62D 57/032 |

(Continued)

OTHER PUBLICATIONS

X. Mu et al. "Sagittal Gait Synthesis for a Five-Link Diped Robot", Proceeding of the 2004 American Control Conference, pp. 4004-4009, Jun. 30-Jul. 2, 2004.*

(Continued)

*Primary Examiner* — Jacqueline Woznicki
(74) *Attorney, Agent, or Firm* — McAndrews, Held & Malloy, Ltd.

(57) ABSTRACT

We present a novel swing phase control module for powered transfemoral prostheses based on minimum jerk theory. The control module allows physiologically appropriate swing movement at any walking speed, regardless of the stance controller action. Preliminary validation in a transfemoral amputee subject demonstrates that the control module provides physiological swing timing, without speed or patient-specific tuning.

15 Claims, 6 Drawing Sheets

(56) References Cited

U.S. PATENT DOCUMENTS

| | | | |
|---|---|---|---|
| 2001/0029400 A1* | 10/2001 | Deffenbaugh | A61F 2/68 623/24 |
| 2004/0049290 A1* | 3/2004 | Bedard | A61F 2/644 623/24 |
| 2006/0122710 A1* | 6/2006 | Bedard | A61F 2/644 623/24 |
| 2007/0050047 A1* | 3/2007 | Ragnarsdottlr | A61F 2/68 623/24 |
| 2010/0113980 A1* | 5/2010 | Herr | A61F 2/60 600/587 |
| 2010/0324699 A1* | 12/2010 | Herr | A61F 2/66 623/27 |
| 2011/0137429 A1* | 6/2011 | Bedard | A61F 2/644 623/24 |
| 2013/0297041 A1* | 11/2013 | Bedard | A61F 2/644 623/24 |
| 2018/0004208 A1* | 1/2018 | Su | B62D 57/032 |
| 2018/0036147 A1* | 2/2018 | Gregg | A61F 2/60 |

OTHER PUBLICATIONS

N. Dong et al. "Piecewise Polynomial Nonlinear Model Reduction", Design Automation Conference, 2003. Proceeedings, pp. 484-489, Jun. 2-6, 2003.*

I. Seleem et al. "A Neuro Fuzzy-Based Gait Trajectory Generator for a Biped Robot Using Kinect Data", 2016 3rd International Conference on Information Science and Control Engineering, pp. 763-768, 2016.*

R. Dehghani et al. "Cyclic gait planning and control of a fice-link biped robot with four actuators during single support and double support phases", Multibody System Dynamics, vol. 33, pp. 389-411, 2015.*

K. Jeon et al. "Optimal Trajectory Generation for a Biped Robot Walking a Staircase based on Genetic Algorithms", Profeedings of 2004 IEEE/RSJ International Conference on Intelligent Robots and Systems, pp. 2837-2842, Sep. 28-Oct. 2, 2004.*

J. Yoon et al. "Optimal Trajecttory Generation of Serially-Linked Parallel Biped Robots", Proceedings of the 2006 IEEE International Conference onf Robotics and Automation, pp. 1610-1615, May 2006.*

* cited by examiner

MINIMUM JERK SWING CONTROL FOR ASSISTIVE DEVICE

CROSS REFERENCE TO RELATED APPLICATIONS

This application is a non-provisional that claims benefit to U.S. Provisional Patent Application No. 62/043,213, filed on Aug. 28, 2014, and U.S. Provisional Patent Application No. 62/049,686, filed on Sep. 12, 2014, both of which are incorporated herein by reference.

FEDERALLY SPONSORED RESEARCH OR DEVELOPMENT

This invention was made with government support under W81XWH-09-2-0020 awarded by the United States Army. The government has certain rights in the invention.

BACKGROUND

Powered prostheses have the potential to improve the walking ability of individuals with transfemoral amputations. However, propulsion of the swing movement is generated entirely by the user, who must pull the thigh forward at the end of stance (i.e., exaggerating the hip flexion torque) to initiate the swing movement. This unnatural action produces an asymmetric gait pattern. Powered prostheses can overcome this limitation by mimicking the action of biological muscles to actively propel and control swing movement. However, attaining biologically accurate swing requires continuous adaptation of swing movement duration with walking speed and cadence. Many powered transfemoral prostheses largely rely on impedance-inspired control, an approach that does not allow direct regulation of swing duration. Impedance inspired control defines joint torque as a parametric function of angle and velocity, with different stiffness, damping, and equilibrium values for each discrete phase of the gait cycle. Swing duration therefore depends on the dynamic interaction of the prosthetic leg with the user and the environment during the swing phase, as well as on leg angle and velocity at the transition between stance and swing phase. Swing trajectory can be modified by regulating the impedance parameters of the prosthesis, though swing duration cannot be defined a priori (i.e., it is not a controlled parameter). Because impedance-inspired control needs user and speed-specific tuning to obtain desired swing duration, variable cadence can be difficult to achieve.

BRIEF SUMMARY

In an embodiment, a method for control of an assistive device is disclosed. The method may comprise computing a first set of coefficients of a first polynomial function, to determine at least one angle position for an ankle joint of the assistive device when the assistive device is in a swing phase, and computing a second set of coefficients of a second polynomial function and a third polynomial function, to determine at least one angle position for a knee joint of the assistive device when the assistive device is in the swing phase.

In an embodiment, the method may further comprise determining the at least one angle position for the knee joint and determining the at least one angle position for the ankle joint. In an embodiment, the method may further comprise setting the ankle joint to the determined ankle position and setting the knee joint to the determined knee position. In an embodiment, the ankle joint and the knee joint are set to their respective determined positions by applying a torque to each joint. In an embodiment, each of the first, second, and third polynomial functions are fifth-order polynomial functions. In an embodiment, the first set of coefficients are computed at least in part on the basis of the position, velocity, and acceleration of the ankle joint at the start of the swing phase. In an embodiment, the first set of coefficients are computed at least in part on the basis of the desired position and acceleration at the end of the swing phase. In an embodiment, the first set of coefficients are computed at least in part on the basis of a desired duration of the swing phase. In an embodiment, the desired duration of the swing phase is determined on the basis of the duration of the immediately prior stance phase of the assistive device. In an embodiment, the desired duration of the swing phase is 0.30 times the duration of the immediately prior stance phase. In an embodiment, the first set of coefficients are computed at least in part on the basis of values set by a clinician and based on the needs of a specific user. In an embodiment, the first set of coefficients are computed at least in part on the basis of the ambulation mode of the prosthesis. In an embodiment, the second set of coefficients are computed at least in part on the basis of a maximum knee flexion position. In an embodiment, the maximum knee flexion position is pre-set. In an embodiment, the maximum knee flexion position is linearly modulated. In an embodiment, the maximum knee flexion position is linearly modulated between 50 and 75 degrees in response to a walking speed. In an embodiment, the maximum knee flexion position is set on the basis of an ambulation mode of the device during the swing phase.

DETAILED DESCRIPTION

We propose a new control approach for swing phase that relies on a minimum jerk trajectory. Using this approach, we can obtain a biologically accurate swing movement with direct control of swing duration that is independent of joint angle and velocity at the stance-to-swing phase transition. Direct control of swing movement duration facilitates natural gait symmetry for any walking speed and cadence. Swing phase duration can be set to be proportional to stance phase duration at each step in order to restore the physiological relationship between the two phases of the gait cycle.

Minimum jerk control can attain biologically appropriate swing movement without subject- or speed-specific tuning. Notably, we can enforce a desired maximum knee flexion in swing phase independent of walking speed and cadence, thus ensuring proper foot clearance in all conditions. Moreover, we can regulate the desired swing terminal angle as needed for walking up or down a ramp, again independently of swing movement duration, without any need for tuning.

Figure 1:
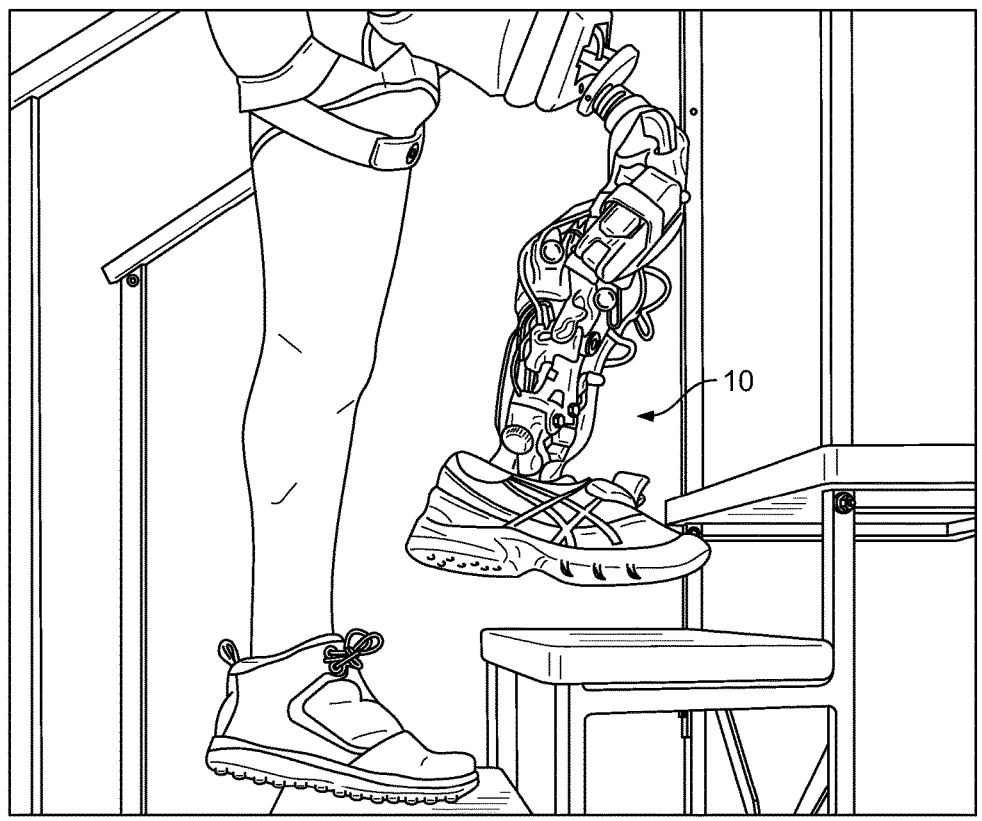
FIG. 1 displays an embodiment of a powered transfemoral prosthesis.

Prosthesis 10 is shown at FIG. 1. Prosthesis 10 may comprise a powered knee, a powered ankle, and a powered shank. The knee and the ankle are each coupled to one or more motors and one or more transmissions that together are capable of producing physiological levels of torque. The motors may be brushless DC motors to deliver biomechanically appropriate torque and power at the knee and ankle joints. Prosthesis 10 and its related powered components are powered by a battery. Although prosthesis 10 is disclosed as an embodiment, other assistive devices, such as orthoses and exoskeletons, may incorporate a control module using the methods described here, including but not limited to the prosthesis described in U.S. Provisional Patent Application No. 62/088,849 to Kuiken et al, titled Powered and Passive Assistive Device and Related Methods, filed Dec. 8, 2014, which is incorporated by reference. Prosthesis 10 further comprises mechanical sensors.

In one embodiment, mechanical sensors include a load cell that measures the vertical load along the long axis of prosthesis 10; a position sensor and a velocity sensor that measure the position and velocity of the knee; a position sensor and a velocity sensor that measure the position and velocity of ankle; and a six degree of freedom inertial measurement unit (IMU) at the shank, comprising accelerometers and gyroscopes for measuring accelerations and angular velocities. Mechanical sensors may be contained within the assembly of prosthesis 10, attached to prosthesis 10, or attached to the user of prosthesis 10. In other embodiments, the knee and ankle could be powered instead with hydraulics, compressed gas, or other mechanisms.

A socket may be used in conjunction with the prosthesis 10. The socket fits onto the residual limb of a user. The socket may comprise a lining and an exterior shell. The prosthesis 10 may be coupled to the socket by a pyramid style connector or other appropriate connector. The socket may be coupled to electrodes. In one embodiment, the electrodes are embedded in the socket and contact the user's skin. The electrodes measure EMG signals from the user's residual limb muscles when the user operates the prosthesis 10. In one embodiment, the electrodes may be placed on the following muscles of the user: semitendinosus, biceps femoris, tensor fasciae latae, rectus femoris, vastus lateralis, vastus medialis, sartorius, adductor magnus, and gracilis.

Figure 6:
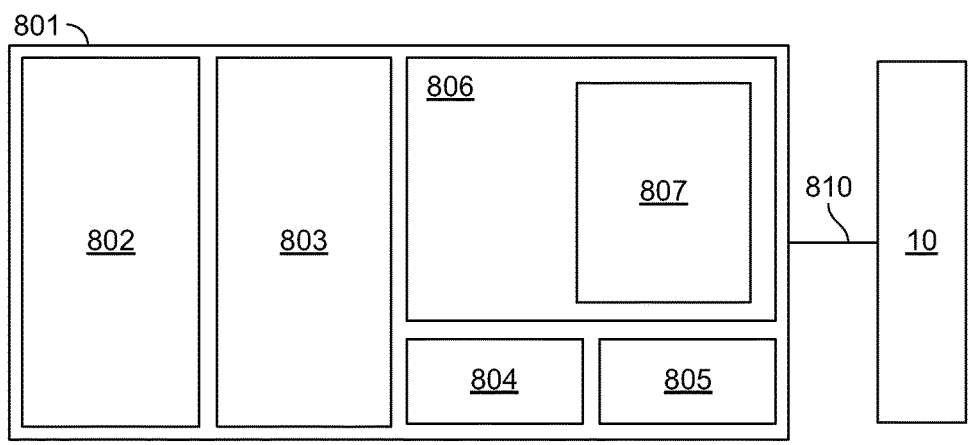
FIG. 6 displays a representation of an embodiment of a controller used to control a prosthesis.

In one embodiment, a controller is physically attached to the socket or other part, such as to the prosthesis 10, and connected to the components of the prosthesis 10 and to electrodes by a communication bus. As shown in FIG. 6, the controller may comprise a controller board 801, which may comprise a microprocessor 802, memory 803, signal filtering hardware 804, and sampling hardware 805. A control module 806 may be programmed onto the controller board 801 and may be executed by the controller board 801, such as by the controller board's microprocessor 802. The control module 806 may comprise a swing phase control module 807. The controller board 801 may communicate with the prosthesis by a bus 810.

An embedded control system may execute a closed-loop torque control modules for the ankle and knee joints. In one embodiment, a remote computer using a hard real-time operative system (xPC target, Mathworks, USA) runs the algorithms for the estimate of gait phase and walking speed, as well as the stance phase and swing phase control modules. Communication between the embedded and remote systems is handled by a high-speed CAN bus (CAN-AC2-PCI, Softing, USA). Communication, processing, and data recording run on the remote control system at the fixed sampling rate of 1 KHz. In another embodiment, the operations of the modules that reside the remote controller shown in FIG. 2 instead may be incorporated into hardware controllers or other control modules attached to the prosthesis 10.

The swing control module 807 may be used to control a transfemoral prosthesis 10, shown at FIG. 1. In an experiment, we evaluated the swing control module 807 in a transfemoral amputee subject walking on a treadmill at three different speeds. The experimental protocol comprised walking with the motorized prosthesis or a prescribed passive prosthesis. Experimental results showed that minimum jerk control allowed biologically appropriate swing movement by automatically adapting swing duration with walking speed and cadence. The subject improved swing timing when using the powered prosthesis compared to using his passive prosthesis. The subject's swing trajectory was smoother when using powered prosthesis than when using his passive prosthesis.

Figure 7:
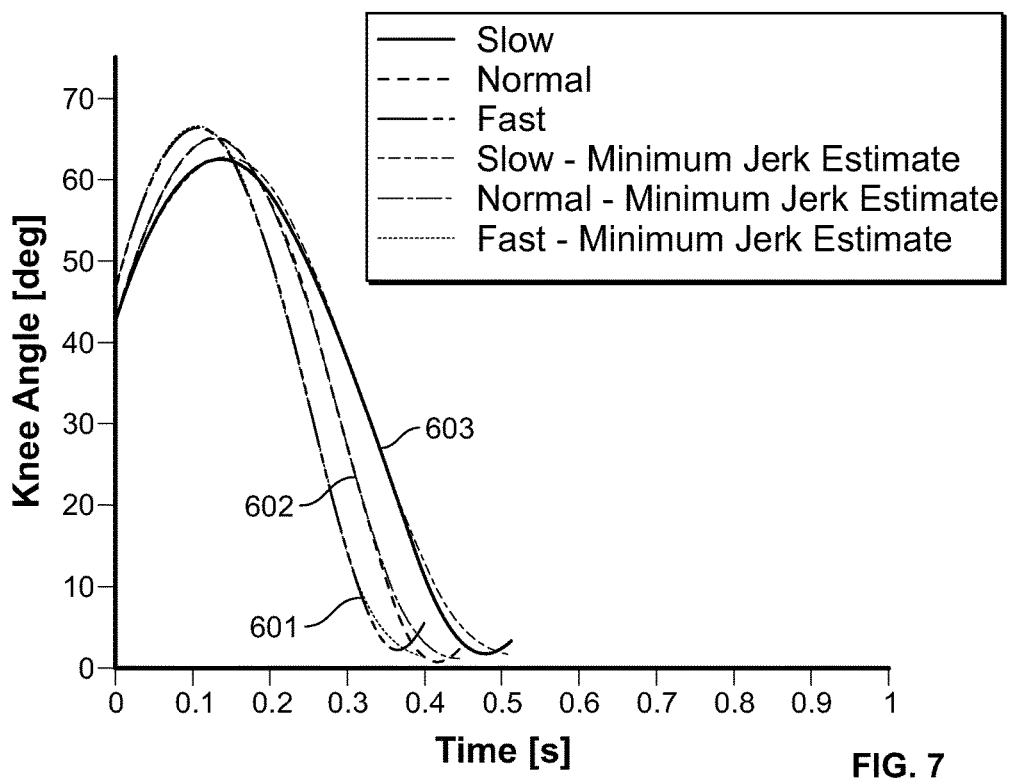
FIG. 7 displays a graph of the knee angle position in degrees during swing phase (in seconds) in certain trials of embodiments of the prosthesis, in comparison to data relating to able-bodied walking.

FIG. 7 displays a graph showing the results of trajectory control with an embodiment of the swing phase control module in the prosthesis 10. Specifically, the curves compare the knee angle position, in degrees, of an able bodied human knee and the knee of the prosthesis 10 over the time period of about 0.3-0.5 seconds that the respective leg is in swing. The two curves 601 compare a fast swing phase of an able bodied human (the solid curve in 601, plotted from able-bodied data from Winter) with a fast swing phase of the prosthesis 10 when employing the swing phase control module (the dotted curve in 601). The two curves 602 compare a normal-speed swing phase of an able bodied human (solid curve in 602) with a normal-speed swing phase of the prosthesis 10 when employing the swing phase control module (dotted curve in 602). The two curves 603 compare a slow swing phase of an able bodied human (solid curve in 603) with a slow swing phase of the prosthesis 10 when employing the swing phase control module (dotted curve in 603). A visual review of each set of curves show that the angle position of the able bodied knee closely matches the angle position of the prosthetic knee throughout the period of swing, at slow, normal, and fast swing speeds.

Figure 2:
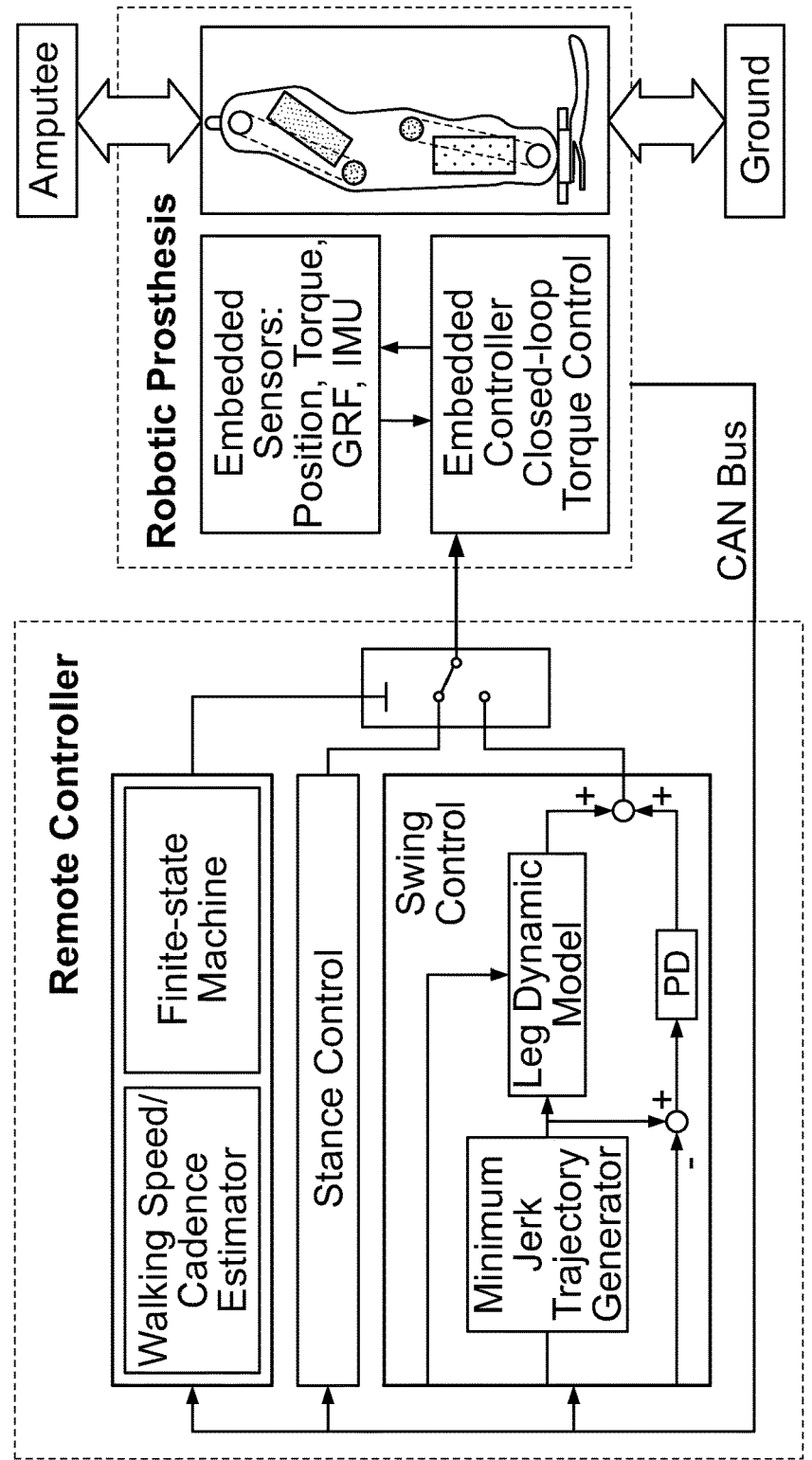
FIG. 2 displays a block diagram of an embodiment of a controller for a prosthesis.

Swing control module design and implementation. A block diagram of a prosthesis swing control module is shown in FIG. 2. The overall control architecture of the prosthesis 10 and its accompanying system for control comprises three stages: (1) identification of user and prosthesis status (i.e., walking speed/cadence estimator, finite-state machine); (2) planning of prosthesis joint torque (i.e., stance and swing phase control modules); and (3) attainment of desired torque in prosthesis joints (i.e., embedded closed-loop control).

Figure 8:
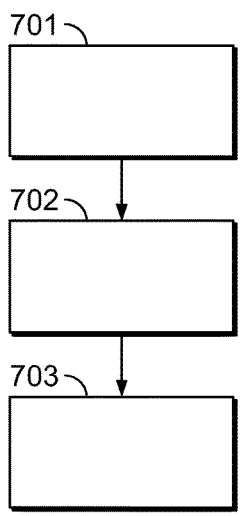
FIG. 8 displays a block representation of a method of operating a prosthesis.

The swing phase control module enforces a minimum jerk position trajectory that approximates the behavior of an intact leg at different walking speeds. FIG. 8 displays a flow chart indicating one method of operation. In 701, the finite-state machine enters into swing mode (i.e., prosthetic foot off the ground). In 702, the swing phase control module computes the desired position trajectory for one or more joints of the prosthesis 10. In 703, the system can enforce the position trajectory determined by the swing phase control module.

Focusing in more detail on step 702, the swing phase control module 807 may compute the desired position trajectory for one or more joints of the prosthesis 10. For example, the swing phase control module 807 may compute the desired position trajectory for the ankle joint of a prosthesis, for the knee joint of a prosthesis, or for the ankle joint and the knee joint. Each joint position trajectory may be computed separately from the other joint position trajectories. Each joint position trajectory may be computed by minimizing jerk, which is the third time derivative of position, along the swing movement execution.

In an embodiment, the swing phase control module 807 minimizes jerk by defining the swing trajectory angle of the joint (referred to here as x(t)) with a $5^{th}$ order polynomial function such as $x(t)=a_0+a_1t+a_2t^2+a_3t^3+a_4t^4+a_5t^5$. Minimum jerk minimization requires the sixth time derivative of the trajectory x(t) to be zero, and that by definition the sixth time derivative of a $5^{th}$ order polynomial function is always zero. Therefore, the swing phase control module 807 obtains minimum jerk trajectories by computing the coefficients a0 to a5 of a $5^{th}$ order polynomial function for each joint of the prosthesis 10, and then solving for the trajectory position at various times t during swing phase. For example, the swing phase control module 807 obtains a minimum jerk trajectory for the ankle joint using a first $5^{th}$ order polynomial function and obtains a minimum jerk trajectory for the knee joint using a second $5^{th}$ order polynomial function.

In an embodiment, the coefficients of the $5^{th}$ order polynomial function for the ankle joint are optimized using a standard optimization module, such as the one described in Computational Neurobiology of Reaching and Pointing A Foundation for Motor Learning, Reza Shadmehr and Steven P. Wise MIT Press, Cambridge, Mass., 2005, incorporated by reference. The optimization module may take the following parameters: measured position, velocity, and acceleration of the ankle joint at the start of swing phase; desired position, and acceleration of the ankle joint at the end of the swing phase; and the desired duration of the swing phase.

The desired position and acceleration of the ankle joint at the end of the swing phase can be pre-set by a therapist or another clinician to constant values. For example, a clinician may set each value to zero, based on the needs of a specific patient or other user. Alternatively, the desired position, and acceleration of the ankle joint at the end of the swing phase may be adapted by the controller of the prosthesis 10, based on the specific ambulation mode of the prosthesis 10 during the swing phase. Such modes may include walking up or down stairs, level walking, or incline walking. For example, the desired position at the end of swing phase can be set to zero degrees for level ground walking or to 5 degree when the prosthesis is an ambulation mode for incline walking, for instance on a ramp.

Certain values related to the control of the prosthesis 10 may be set by a therapist or other clinician. They may be set through a computing device in communication with the prosthesis 10 and/or the controller 801. They may be set through input features on the prosthesis 10 and/or the controller 801. They also may be set in other manners known to those skilled in the art. Additionally, other values related to the control of the prosthesis 10, such as position, velocity, and acceleration, may be determined by one or more sensors attached to the prosthesis 10, as would be understood by those skilled in the art. Yet other values related to the control of the prosthesis 10, such as the ambulation mode of the prosthesis 10, may be sent by the controller 801 in response to information from sensors attached to the prosthesis 10.

In an embodiment, the desired duration of the swing phase could be pre-set by a clinician to be a constant value. For example, it can be set to be always 0.3 s. In another embodiment, the duration of the swing phase can be set to be proportional to a prior stance phase duration. For example, it can be set to be 0.30 times the immediately prior stance duration, to match the timing observed on healthy individuals as shown in Winter. By setting swing phase duration proportional to the prior stance phase duration, the swing phase duration is adapted so that physiological gait symmetry (i.e. the relative duration of stance and swing phase in a stride) is restored at different walking speed and cadences. In yet another embodiment, the desired duration of the swing phase can be adapted depending on the specific ambulation mode of the prosthesis 10.

In an embodiment, the position of the knee of the prosthesis 10 during swing phase may be determined on the basis of two polynomial functions, rather than a single polynomial function used to determine the ankle position as described above. Each polynomial function may be a fifth-order polynomial function. In an embodiment, the coefficients of the first polynomial function used to determine the knee position during swing is defined by the period from the end of the immediately previous stance phase of the prosthesis 10 to the point of maximum knee flexion with zero velocity. The coefficients of the second polynomial function may be defined by the period from the same maximum knee flexion to the knee at a desired position with zero velocity and acceleration. For example, the desired position may be full extension of the knee. The acceleration at maximum knee flexion may be optimized based on able-bodied data, for instance from the Winter reference. The duration of each period may be fixed, may be set proportional to the previous stance duration, or may be determined on the basis of the ambulation mode of the prosthesis 10.

In an embodiment, the maximum knee flexion position value can be pre-set to a specific value by a clinician. (As used herein, "pre-set" means the value is set before the user ambulates in swing mode. For instance, this may take place in a clinic visit prior to the user using the prosthesis 10.) Alternately, the maximum knee flexion position value may be adjusted during gait, for instance at each step, on the basis of the user's walking speed or cadence. For example, during walking, the maximum knee flexion position may be linearly modulated between 50 and 75 degrees, based on the user's walking speed. In this example, the maximum knee flexion position could be set to 50 degrees when the user's walking speed is 0.5 meters per second or slower, 75 degrees when the user's walking speed is 1.75 m/s or higher, and set to a linearly proportional angular value in between these two walking speeds. In another embodiment, the maximum knee flexion value may be set at each step of the prosthesis 10, based on the orientation of the user's thigh as the prosthesis 10 transitions between stance and swing. For example, the maximum knee flexion value can be set to zero degrees when the thigh orientation in the sagittal plane is 0 degrees or lower, 75 degrees when the thigh orientation is 20 degrees or higher, and linearly modulated in between these two thigh orientation values. In another embodiment, the maximum knee flexion value may be set on the basis of the ambulation mode of the prosthesis 10 during the swing phase. For example, the maximum knee flexion value may be set to 60 degrees for level ground walking, to 95 degrees for stairs climbing, and to other appropriate values for other ambulation modes. The maximum knee flexion angle may be regulated based on user anthropometry to ensure an appropriate foot clearance despite the fixed shank length of the prosthesis.

The desired angular trajectory may be enforced by using feed-back position control such as PID regulator. Alternatively, the desired angular trajectory can be enforced by relying on the sum of a feed-forward torque command and a feedback position control, such as a PID regulator. The feedforward torque command may be computed with a dynamic model of the prosthesis such as a second order system (mass-spring-damper) model. This model takes as input the desired position, velocity and acceleration during swing movement and computes the joint torque command that would be necessary to drive the dynamic model of the leg on the desired trajectory. Therefore, the feedforward command takes into account accounts for the inertial, gravitational, and frictional torque necessary to perform the swing movement. On the contrary, the feedback loop provide a torque command based on the error between the desired and the measured joint position as defined by a PID regulator. Therefore, the feedback loop allows accommodation to the contingent disturbances that occur during swing phase movement, and, compensates for possible inaccuracies of the prosthesis dynamic model.

As a preliminary evaluation, we tested the proposed control modules on a transfemoral amputee patient (30 years old, 1.86 m, 86.2 Kg). A certified prosthetist fit the subject with the prosthesis 10. The subject then practiced walking with the prosthesis on a treadmill for about 30 minutes at different speeds. After this familiarization phase, we assessed the self-selected speed, which was 0.85 m/s and defined the low and high speed for the main experiment as 0.70 and 1.0 m/s respectively. The patient performed three two-minute sessions at each previously selected walking speed, with at least two minutes of rest between each session. The subject then repeated the test using his prescribed prosthesis (an Elite blade foot and a KX06 knee, Endolite, Miamisburg, Ohio), to which we added sensors—electromechanical goniometers and a foot-switch sensor—to record ankle and knee joint angle, as well as heel and toe contact with the ground. Prosthesis angle profiles were recorded using the sensors located on the prosthesis. Joint velocity and acceleration were obtained in post-processing. To attenuate the sensor noise for proper data analysis, we low-pass filtered all data using a back and forth low-pass first-order Butterworth filter with cutoff frequency of 10 Hz. For each walking speed, we separated raw data into strides (i.e., the time interval between two consecutive heel-strike events on the prosthesis side) using the output of the local ground reaction force sensor for the robotic prosthesis and the foot-switch sensors for the passive prosthesis. Within each stride, we computed the duration of stance-phase, swing-phase, and stride. The first and final three strides for each walking session were omitted from the analysis to avoid including non-steady state walking. Finally, we computed the angle, velocity, and acceleration profiles for the ankle and knee joint averaged over all the steady-state strides recorded at each constant walking speed. Only the third repetition for each walking speed was considered in the analysis, to avoid adaptation effects. All data processing was performed using Matlab (The MathWorks, Natick, Mass., USA).

Figure 3:
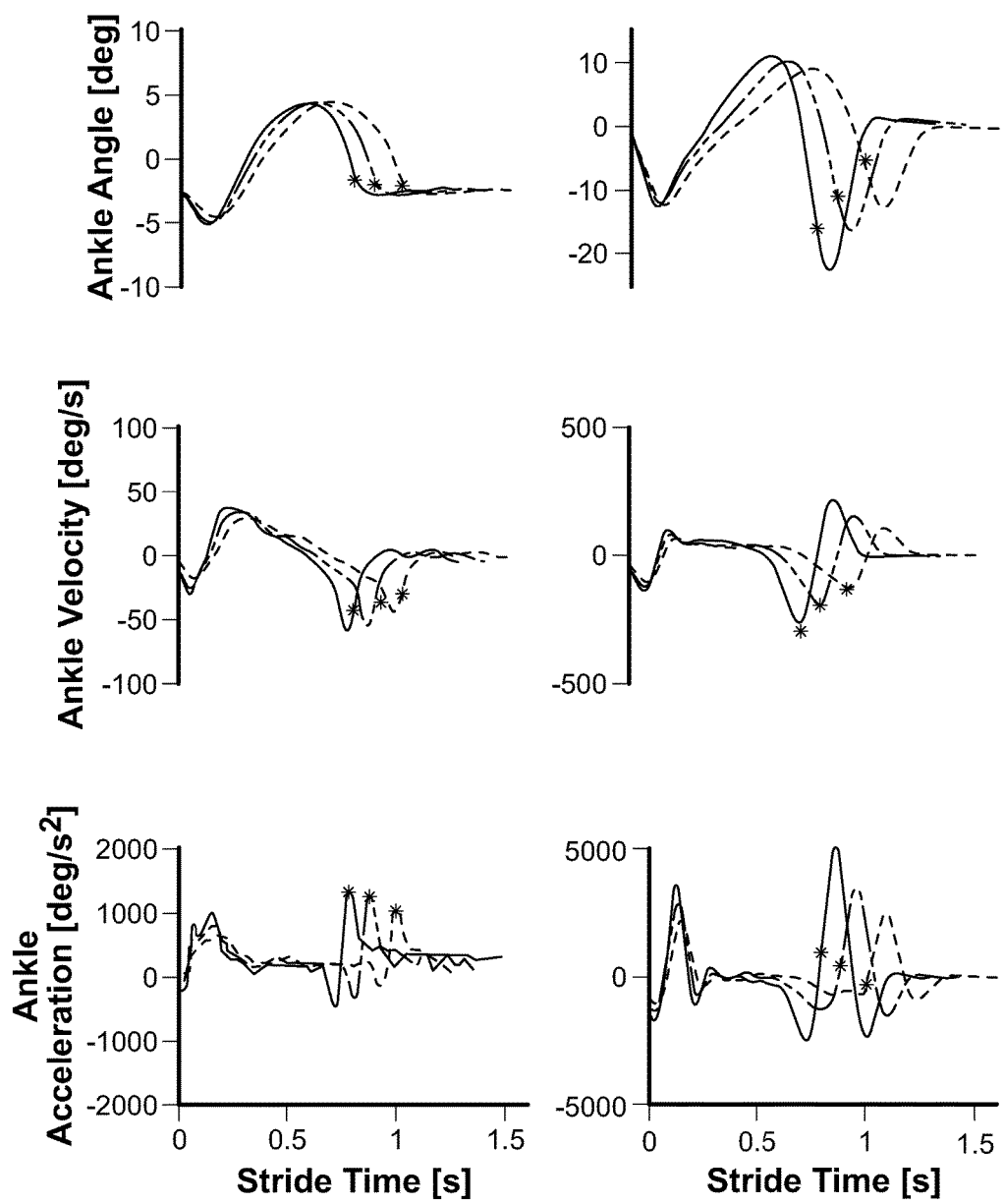
FIGS. 3 and 4 display charts of angle, velocity, and acceleration of test subjects using the features described herein.
Figure 4:
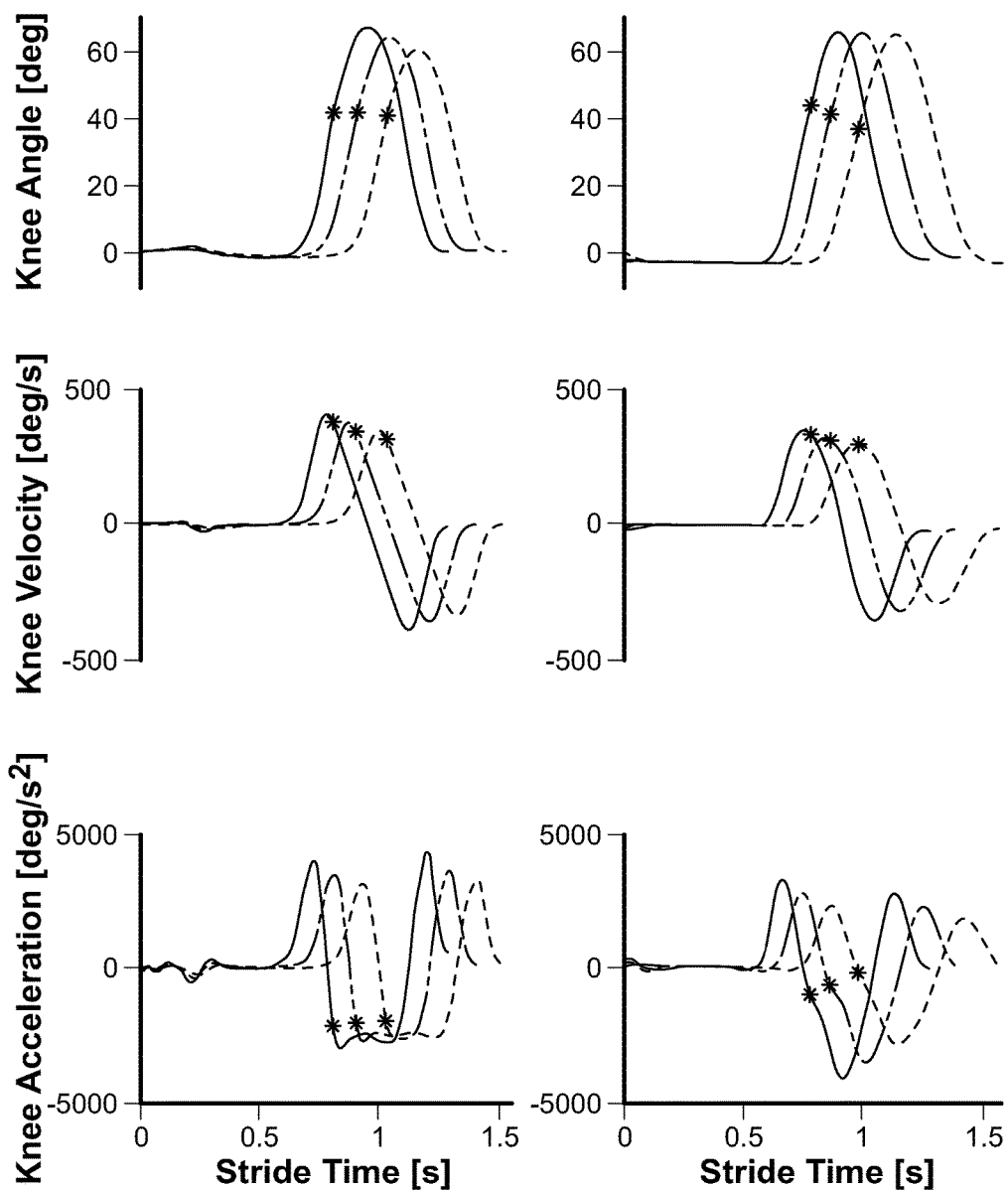

FIG. 3 and FIG. 4 show the angle, velocity, and acceleration profiles averaged over all the strides recorded at the same walking speed for the ankle and knee, respectively. Solid lines indicate the averaged profiles; shaded areas represent +/−one standard deviation. Different lines indicate different walking speeds. Markers show the average transition times from stance to swing phase. The powered ankle kinematics largely differed from those of the passive ankle (FIG. 3). During stance phase, the passive ankle was generally stiffer than the powered ankle and did not provide plantarflexion movement in late stance. This difference is due to the stance phase control module, and thus is not further discussed here. Importantly, the powered ankle movement in swing phase was automatically adapted to walking speed in order to complete the dorsiflexion movement in a physiologically appropriate time. The dorsiflexion movement was completed in a shorter time at higher walking speeds, despite the increased plantarflexion angle and velocity at the transition between stance and swing phase, which was due to speed-dependent action of the stance control module.

Knee kinematics (FIG. 4) were also significantly different between the passive and powered prostheses. The maximum knee flexion angle was independent of walking speed for the powered prosthesis, whereas it increased with walking speed for the passive prosthesis. This indicates that the passive prosthesis failed to fully compensate for the increased momentum of the prosthetic leg, caused by a higher knee flexion speed at the start of swing phase.

Focusing on knee extension, we noted that the powered prosthesis completed the swing movement (i.e., knee velocity reached zero) equally in advance of the end of swing phase for all walking speeds. On the other hand, with the passive prosthesis, the time lapse between the end of knee extension and the end of swing phase varied with walking speed: Whereas at slow speed (green line), the knee extension movement was completed well in advance of the end of swing phase (i.e., the subject waited with the prosthetic knee fully extended before contacting the ground), at the highest speed (blue line), the knee extension coincided with the end of swing phase (i.e., knee velocity just reached zero when the foot contacted the ground). This analysis indicates that using the passive prosthesis provided a much more limited control of swing movement; the fastest possible swing movement was reached at the highest speed of the test (i.e., 1.0 m/s).

The averaged knee velocity peaks were slightly smaller for the motorized prosthesis. In the first part of swing phase, the passive prosthesis had a constant negative acceleration that decelerated the initial knee flexion movement and accelerated the subsequent knee extension movement. This negative acceleration was equal for all walking speeds. Toward the end of swing phase, the acceleration became positive, showing a bell-shaped profile with a peak proportional to walking speed. The powered prosthesis showed instead a smoother acceleration trajectory, with a bell-shape profile during both the negative and positive acceleration phases and peaks proportional to walking speed. A smoother swing was obtained for all walking speeds using the powered prosthesis.

Figure 5:
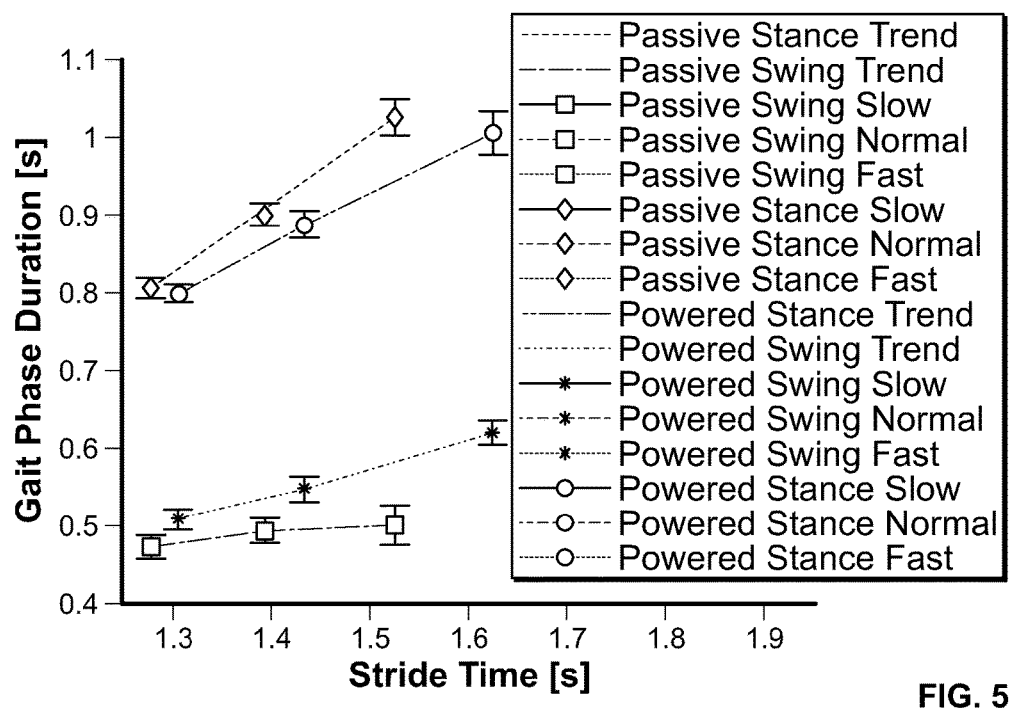
FIG. 5 displays a graph of the stance and swing phase duration for both passive and powered prosthesis for all walking speeds, as a function of stride duration.

FIG. 5 shows the stance and swing phase duration for both passive and powered prosthesis for all walking speeds, as a function of stride duration. When walking with the powered prosthesis, the stride duration was longer, though the difference decreased with walking speed (0.10, 0.04, and 0.02 s for 0.7, 0.85 and 1.0 m/s, respectively). This indicates that the subject took longer steps with the powered prosthesis, possibly better approximating able-bodied behavior. With the powered prosthesis, swing duration was 38.3%, 38.2%, and 38.4% of stride duration for high, normal, and low walking speed, respectively. In contrast, swing duration with the passive prosthesis equaled 36.7%, 35.2%, and 32.8% of stride duration for the same three walking speeds, respectively. The proposed control module achieved physiological swing duration regardless of the walking speed, outperforming the passive device. In contrast to impedance-inspired control, the proposed control module achieved biologically accurate stance and swing timings at any speed without the need for tuning.

We present and validate a novel control module for the swing phase of a motorized prosthesis. Using a principle of minimum jerk, it was possible to provide direct control of swing movement duration. This allows us to set a simple rule to normalize the stance-swing proportion inside each gait cycle, regardless of the walking speed. Experimental results showed that this simple control improved swing timing in a transfemoral amputee using the powered prosthesis when compared to using a passive prosthesis.

What is claimed is:

1. A method for control of an assistive device, comprising:
    a. computing a first set of coefficients of a first polynomial function, to determine at least one angle position for an ankle joint of the assistive device when the assistive device is in a swing phase;
    b. computing a second set of coefficients of a second polynomial function and a third set of coefficients of a third polynomial function, to determine at least one angle position for a knee joint of the assistive device when the assistive device is in the swing phase;
    c. determining the at least one angle position for the knee joint and determining the at least one angle position for the ankle joint; and
    d. setting the ankle joint to the determined ankle position and setting the knee joint to the determined knee position;
    wherein the second polynomial function determines the angle position for the knee joint during a first portion of the swing phase and the third polynomial function determines the angle position for the knee joint during a second portion of the swing phase;
    wherein the first portion of the swing phase is defined by a period from the beginning of the swing phase to a maximum knee flexion position; and
    wherein the second portion of the swing phase is defined by a period from the end of the first portion of the swing phase to the end of the swing phase.

2. The method of claim 1, wherein the ankle joint and the knee joint are set to their respective determined positions by applying a torque to each joint.

3. The method of claim 1, wherein each of the first, second, and third polynomial functions are fifth-order polynomial functions.

4. The method of claim 1, wherein the first set of coefficients are computed at least in part on the basis of the position, velocity, and acceleration of the ankle joint at the start of the swing phase.

5. The method of claim 1, wherein the first set of coefficients are computed at least in part on the basis of the desired position and acceleration at the end of the swing phase.

6. The method of claim 1, wherein the first set of coefficients are computed at least in part on the basis of a desired duration of the swing phase.

7. The method of claim 6, wherein the desired duration of the swing phase is determined on the basis of the duration of the immediately prior stance phase of the assistive device.

8. The method of claim 7, wherein the desired duration of the swing phase is 0.30 times the duration of the immediately prior stance phase.

9. The method of claim 1, wherein the first set of coefficients are computed at least in part on the basis of values set by a clinician and based on the needs of a specific user.

10. The method of claim 1, wherein the first set of coefficients are computed at least in part on the basis of an ambulation mode of the assistive device.

11. The method of claim 1, wherein the second set of coefficients are computed at least in part on the basis of the maximum knee flexion position.

12. The method of claim 11, wherein the maximum knee flexion position is pre-set.

13. The method of claim 11, wherein the maximum knee flexion position is linearly modulated.

14. The method of claim 13, wherein the maximum knee flexion position is linearly modulated between 50 and 75 degrees in response to a walking speed.

15. The method of claim 11, wherein the maximum knee flexion position is set on the basis of an ambulation mode of the device during the swing phase.

* * * * *